United States Patent [19]
Antoshkiw

[11] 4,188,949
[45] Feb. 19, 1980

[54] SEQUENTIAL INJECTION SYRINGE

[75] Inventor: William T. Antoshkiw, Clifton, N.J.

[73] Assignee: Becton, Dickinson & Company, Rutherford, N.J.

[21] Appl. No.: 812,765

[22] Filed: Jul. 5, 1977

[51] Int. Cl.² .............................................. A61M 5/00
[52] U.S. Cl. ............................. 128/218 M; 128/272.1
[58] Field of Search ........ 128/218 M, 218 P, 218 PA, 128/218 R, 272, 272.1, 234

[56] References Cited

U.S. PATENT DOCUMENTS

| | | | |
|---|---|---|---|
| 3,016,896 | 1/1962 | Van Sickle | 128/218 P |
| 3,370,754 | 2/1968 | Cook et al. | 128/218 M |
| 3,477,432 | 11/1969 | Shaw | 128/272.1 X |
| 3,511,239 | 5/1970 | Tuschhoff | 128/218 M |
| 3,570,486 | 3/1971 | Engelsher et al. | 128/218 M |
| 3,705,582 | 12/1972 | Stumpf et al. | 128/218 P |
| 3,749,084 | 7/1973 | Cucchiara | 128/218 R |
| 3,766,917 | 10/1973 | Wimmer | 128/218 M |

*Primary Examiner*—John D. Yasko

[57] ABSTRACT

A syringe for sequentially injecting at least two volumes of liquid with a minimum amount of intermixing prior to and during injection. This is accomplished by means of concentric plunger rods attached, respectively, to adjacent coaxial plungers. A first chamber is filled by drawing back on one plunger, and drawing the liquid through a communicating channel in the other plunger. When the first chamber has been filled to the desired capacity, a second chamber is filled by drawing back on this other plunger. The injection process reverses the previous filling stages, with the most forward plunger being depressed first to inject the fluid in the second chamber adjacent to the tip of the syringe, and the other plunger then being depressed to inject the contents of the first chamber through the communicating channel of the forward plunger and the tip of the syringe.

11 Claims, 9 Drawing Figures

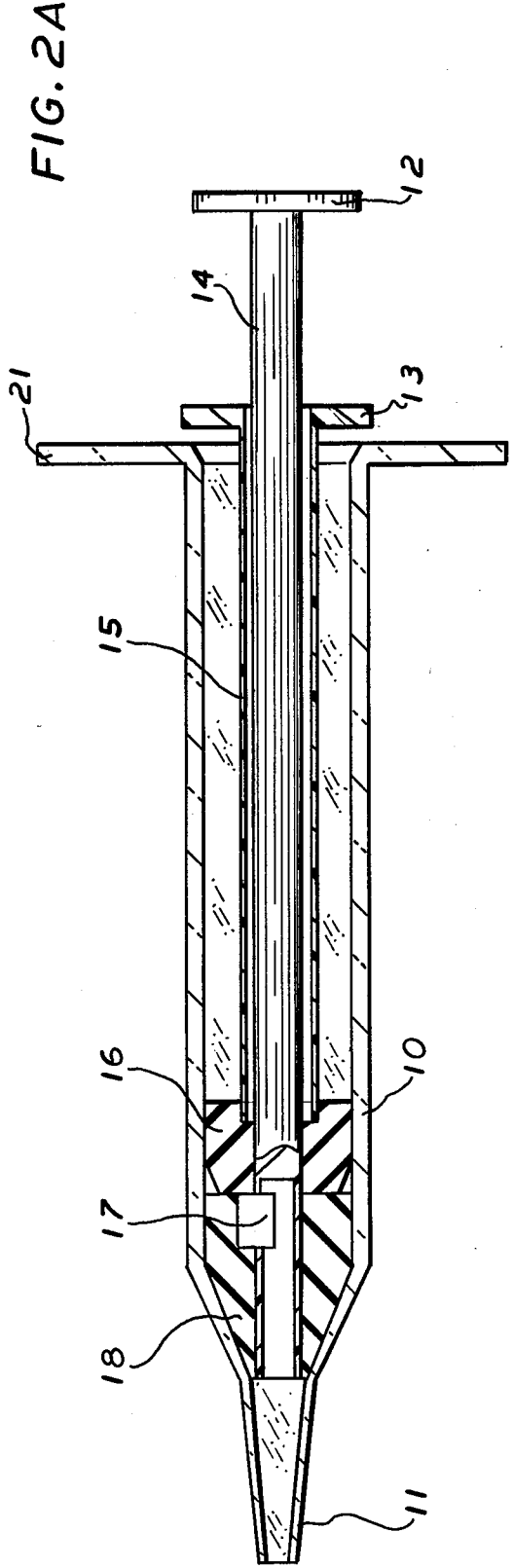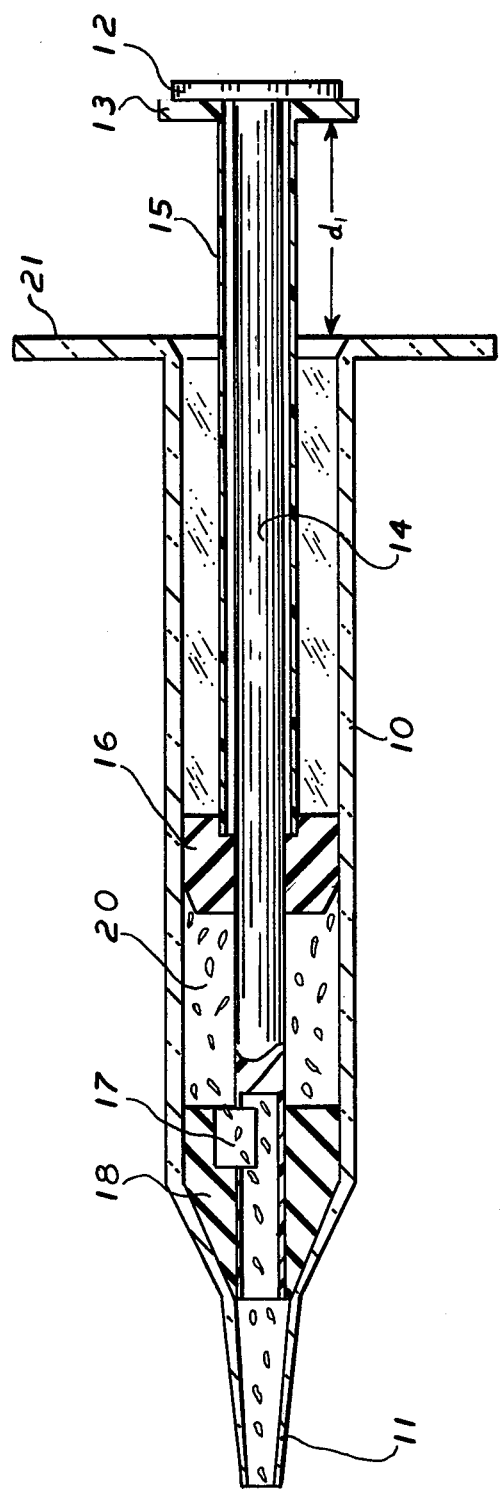

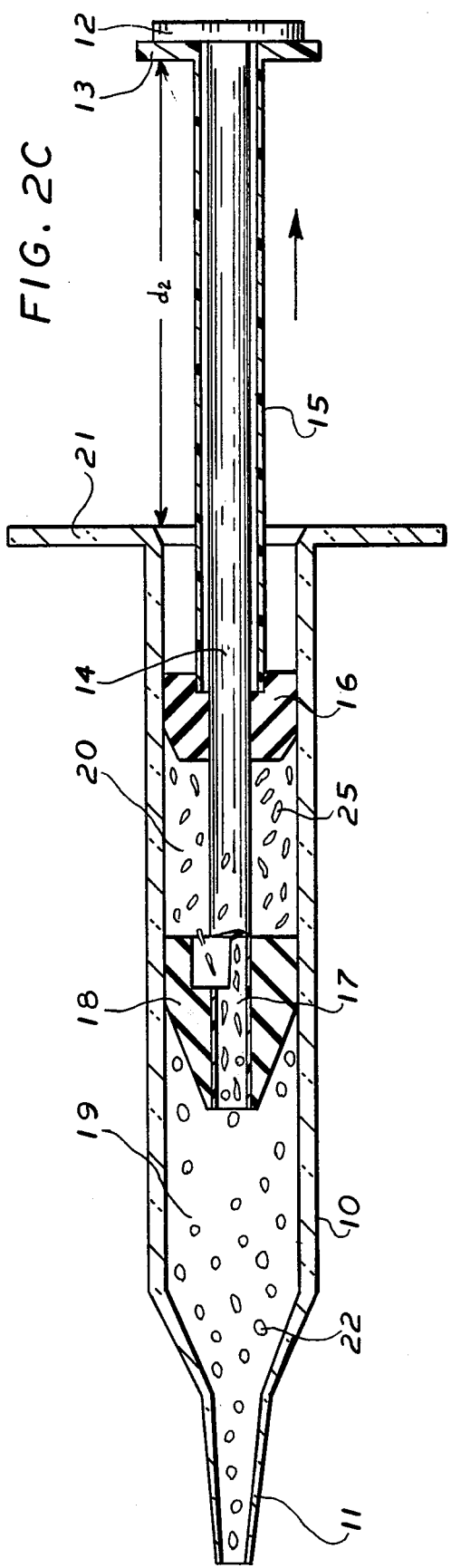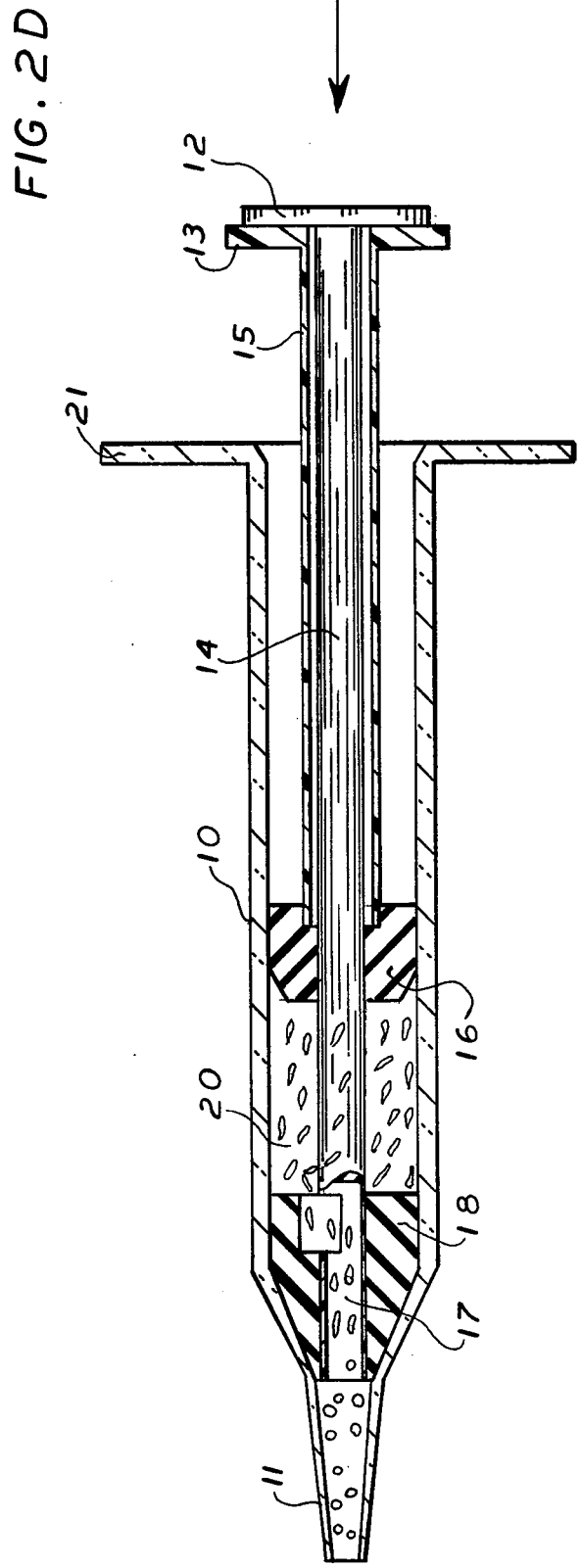

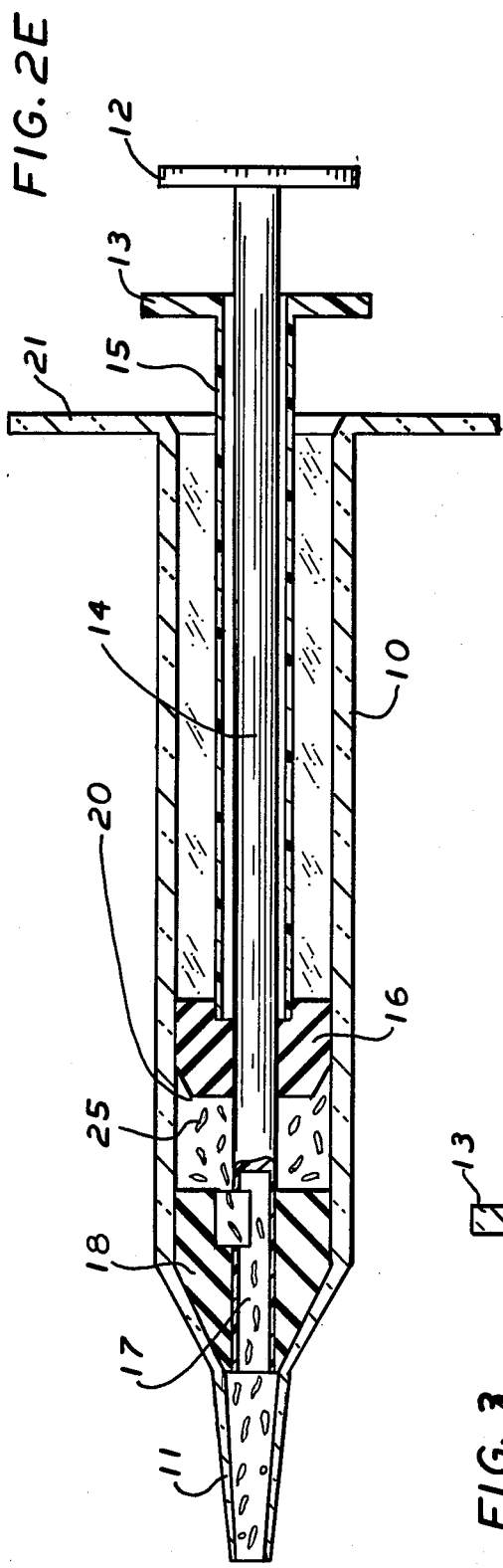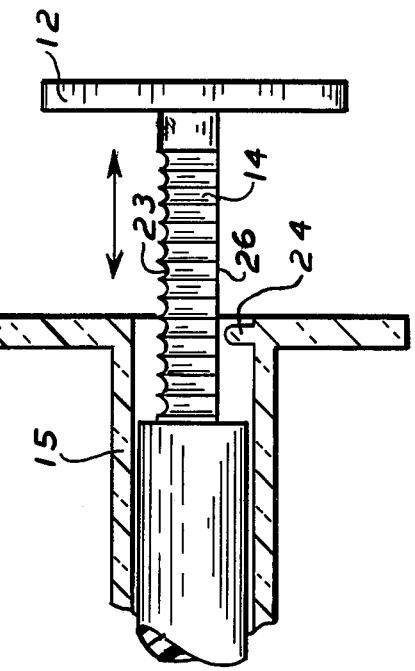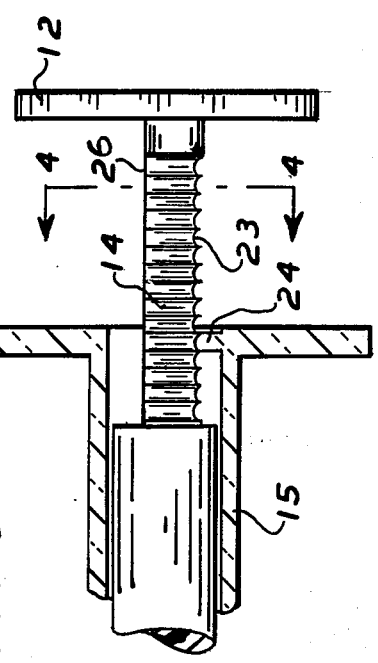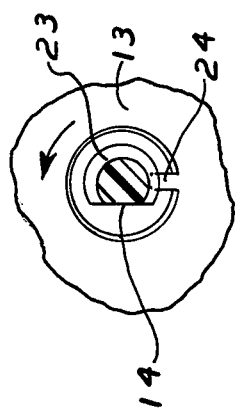

SEQUENTIAL INJECTION SYRINGE

BACKGROUND OF THE INVENTION

The invention relates to a syringe which will accomplish the sequential injection of at least two volumes of liquid with a minimal amount of mixing prior to and during injection.

In the prior art, the injection of specific volumes of two medicaments could be accomplished without substantial intermixing if two syringe assemblies were used. This could be inconvenient for both doctor and patient, and time consuming. Multiple compartment syringes are known to the art, but most of these are designed to mix their separated components prior to or during injection. Valves or plugs with puncture means are often used to separate the chambers thus complicating the structure and operation of these devices.

The injection of radioisotopes into a patient for diagnostic or therapeutic purposes may also present problems. Once the injection has been made, it is desirable to remove the residual radioactive contents from the syringes simply so as to avoid contamination. If a conventional syringe is used, it must be refilled and then injected in order to flush the contents from the device. Once the empty syringe is placed down after use, it would be easy to forget to remove the radioactive material. However, if another liquid is already present in the syringe for this purpose, it would remind the doctor or technician to flush the device and provide an efficient means for doing so.

SUMMARY OF THE INVENTION

It is an object of the invention to provide an effective and easily operable device whose purpose is to sequentially inject at least two volumes of liquid with a minimum amount of intermixing prior to and during injection. This is accomplished by means of at least two concentric plunger rods to which coaxial plungers are attached. One plunger is drawn back, thereby drawing liquid through a passage in the other plunger and into a chamber. Once this chamber has been filled to the desired capacity, the second plunger is pulled back to draw liquid into another chamber.

The injection process merely reverses the previous filling operation. The second plunger, which is nearest the tip of the syringe, is depressed to inject the contents of the last filled chamber. Injection of the contents of the first filled chamber is accomplished by depressing the first plunger.

It can be seen that the filling and injection processes are similar to conventional single chamber methods, which is an object of the invention. The device is accordingly operated without difficulty or complication by medical personnel. Additional plungers may be employed to define further chambers within the barrel, and so allow the injection of additional fluids.

It is another object of the invention to provide a means for injecting a plurality of medicaments into a patient without the need for a plurality of punctures by hypodermic needles.

Still another object of the invention is to provide a time saving and efficient means for flushing a syringe after it has been used to inject radioactive substances.

Other objects and advantages will become apparent from the following detailed description which is taken in conjunction with the accompanying drawings.

BRIEF DESCRIPTION OF THE DRAWINGS

FIG. 2A is a sectional view of the syringe taken along the lines A—A of FIG. 1. The plungers are positioned in preparation to the filling operation.

FIG. 2B is a similar view after the first plunger has been drawn to fill the first chamber.

FIG. 2C is a similar view after the second plunger has been drawn to fill the second chamber.

FIG. 2D is a similar view, showing the injection of liquid from the second chamber in a substantially unmixed condition by moving the second plunger forward.

FIG. 2E is a similar view showing the injection of liquid from the first chamber in a substantially unmixed condition by forward movement of the first plunger.

FIG. 3 shows another embodiment of the invention, wherein the plunger rods are provided with an interlocking mechanism.

FIG. 4 shows the relative rotation of the plunger rods to either lock or unlock the two rods.

FIG. 5 shows the rods in an unlocked position.

DETAILED DESCRIPTION OF THE PREFERRED EMBODIMENT

Figure 1:
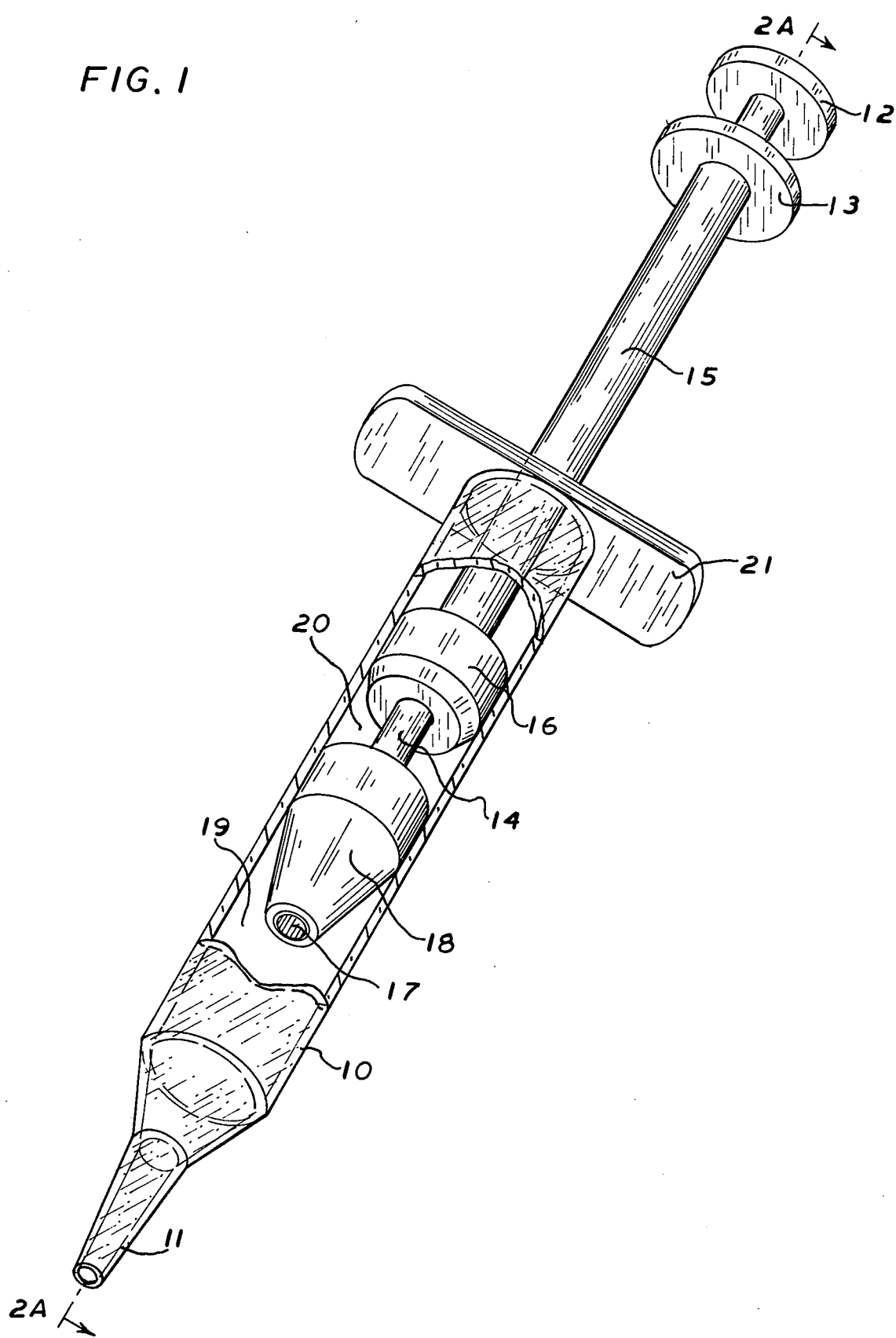
FIG. 1 is a perspective view of the syringe with a section of its wall removed so as to show the coaxial plungers and concentric plunger rods.

In the drawings, the syringe is shown in an empty condition in FIG. 1. In order to fill it with a liquid, the first plunger 16 and second plunger 18 must first be positioned as shown in FIG. 2A.

FIGS. 2A-E show the stages of operation of the syringe 10. After the plungers are positioned according to the assembly of 2A, plunger 16 is drawn by pulling a handle member 13 which is connected by plunger rod 15. Liquid 25 is thereby drawn through the tip 11 of the syringe to the channel 17 in the second plunger 18. The channel is in flow communication with the first chamber 20 which will hold the liquid so drawn.

To fill the second chamber 19, flanges 12 and 13 are pulled so as to move plunger 18 away from tip 11. FIG. 2C shows plunger rod 14 to be concentric with rod 15, and movement of this connection means 14 pulls plunger 18 so as to create a second chamber 19 between it and tip 11. Chamber 20 will be positioned further back due to this procedure and the incompressibility of most liquids, and the distance d2 between flange 21 and flange 13 will be greater than distance d1 as shown in FIG. 2B. The second liquid 22 will occupy this chamber 19.

Injection of the fluids without substantial mixing thereof is shown in FIGS. 2D and 2E. Member 12 is pushed forward so as to inject liquid 22 through the tip of the syringe. Plunger 18 is moved until it contacts the tip, whereupon substantially all of liquid 22 is expelled.

At this point, plunger 16 will be moved until it contacts the second plunger 18. Substantially unmixed liquid 25 will pass through channel 17 and out of the syringe.

To insure simultaneous movement of plungers 16 and 18 during the filling or injection of chamber 19 a mechanical coupling mechanism, either positive or frictional, can be designed into the plunger assembly.

Towards this end, plunger 16 is designed so as to exert compression forces upon first plunger rod 14. Because the plungers are of rubber or other resilient material, a tight fit of plunger 16 over rod 14 will insure the frictional forces necessary to move both plungers and rods simultaneously.

Alternatively, a positive interlocking mechanism that would couple the plunger rods may also be used. As shown in FIGS. 3–5, the inner plunger rod 14 may contain circumferential grooves 23, and the outer rod 15 a locking tab 24 which locks into the grooves. The locking tab is released by rotating either the inner or outer plunger rod so that the tab overlies flattened section 26, and is not within any groove.

The above mechanisms insure the simultaneous movement of the plungers even when flanges 12 and 13 are not adjacent to one another as in FIG. 2C.

The above desciption is intended to be illustrative and not limiting, and the scope of the invention is to be determined in light of the appended claims.

What is claimed is:

1. A syringe capable of sequentially injecting at least two volumes of liquid with a minimum amount of intermixing prior to and during injection comprising:
   a. a barrel having a forward end and rear end;
   b. at least two plungers in the barrel including a first plunger between the forward and rear ends of the barrel, and a second plunger between said first plunger and the forwward end;
   c. an opening to permit the passage of liquid at the forward end of the barrel;
   d. a passage for directing a first liquid between the first and second plungers upon withdrawal of the first plunger towards the rear end of the barrel, and in flow communication with the opening in the barrel; and
   e. plunger actuating means, allowing a first liquid to be drawn between the first and second plungers upon withdrawal of the first plunger towards the rear end of the barrel, and a second liquid to be drawn between the forward end of the barrel and the second plunger upon withdrawal of the second plunger towards the rear end of the barrel.

2. A syringe as defined in claim 1 in which the plunger actuating means comprises concentric plunger rods attached to each of the plungers, respectively.

3. A syringe as defined in claim 2 in which a mechanical coupling mechanism is provided to insure the simultaneous movement of the plungers.

4. A syringe as defined in claim 3 in which the coupling is accomplished by means of the frictional engagement of the first plunger and the inner plunger rod, said inner plunger rod being attached to the second plunger.

5. A syringe as defined in claim 1 in which the passage for directing fluid between the first and second plungers is a conduit within the second plunger.

6. A syringe as defined in claim 1 in which the hypodermic needle is attached to the open end of the syringe barrel.

7. A syringe as defined in claim 2 wherein the plunger rods have flanges to facilitate their manipulation.

8. A syringe capable of sequentially injecting at least two volumes of liquid with a minimum amount of intermixing prior to and during injection comprising:
   a barrel having a forward end and a rear end;
   at least two plungers in the barrel including a first plunger between the forward and rear ends of the barrel, and a second plunger between said first plunger and the forward end;
   an opening to permit passage of liquid at the forward end of the barrel;
   a passage for directing a first liquid between the first and second plungers upon withdrawal of the first plunger towards the rear end of the barrel, and in flow communication with the opening in the barrel;
   plunger actuating means, allowing a first liquid to be drawn between the first and second plungers, and a second liquid to be drawn between the forward end of the barrel and the second plunger, said plunger actuating means comprising concentric plunger rods attached to each of the plungers, respectively; and
   a mechanical coupling mechanism adapted to provide simultaneous movement of the plungers, the inner plunger rod including circumferential grooves and the outer rod and a locking tab designed to fit within the grooves.

9. A syringe described in claim 8 wherein the inner plunger includes a flattened section opposite said circumferential grooves whereby the tab may be released from said grooves upon rotation of either plunger rod.

10. A syringe as described in claim 3 wherein one of said plunger rods includes circumferential grooves and the other of said plunger rods a locking tab designed to fit within said grooves.

11. A syringe as described in claim 10 wherein said plunger having circumferential grooves also includes a flat section opposite said grooves whereby the tab may be released from said grooves upon rotation of other plunger rod.

* * * * *

UNITED STATES PATENT AND TRADEMARK OFFICE
CERTIFICATE OF CORRECTION

PATENT NO. : 4,188,949
DATED : February 19, 1980
INVENTOR(S) : William T. Antoshkiw It is certified that error appears in the above-identified patent and that said Letters Patent are hereby corrected as shown below:

Claim 1, column 3, line 25, "forwward" should be --forward--.

Signed and Sealed this

Twenty-ninth Day of July 1980

[SEAL]

Attest:

SIDNEY A. DIAMOND

Attesting Officer

Commissioner of Patents and Trademarks